United States Patent [19]

Holland

[11] Patent Number: 5,248,292
[45] Date of Patent: Sep. 28, 1993

[54] STATIC ORTHOSIS FOR ACCOMPLISHING PROGRESSIVE EXTENSION OF A LIMB

[76] Inventor: Marlan J. Holland, P.O. Box 2770, Atascadero, Calif. 93423

[21] Appl. No.: 987,170

[22] Filed: Dec. 7, 1992

[51] Int. Cl.$^5$ ............................................. A61F 5/00
[52] U.S. Cl. ........................................ 602/6; 602/5; 602/20; 602/23; 602/62
[58] Field of Search .................. 602/1, 5, 6, 20, 21, 602/23-26, 60, 61, 62; 128/845, 846, 878, 882

[56] References Cited

U.S. PATENT DOCUMENTS

| | | | |
|---|---|---|---|
| 2,868,193 | 1/1959 | Kreft | 602/6 |
| 3,850,167 | 11/1974 | Seeley | 602/6 |
| 3,942,522 | 3/1976 | Kinnier Wilson | 602/14 X |
| 4,111,194 | 9/1978 | Cox et al. | 602/26 |
| 4,768,500 | 9/1988 | Mason et al. | 602/26 |
| 4,905,715 | 3/1990 | Johnson | 602/23 X |
| 4,941,460 | 7/1990 | Working | 602/21 |
| 4,986,266 | 1/1991 | Lindemann | 602/24 X |
| 5,007,415 | 4/1991 | Marion | 602/26 |
| 5,058,576 | 10/1991 | Grim et al. | 602/21 |
| 5,069,203 | 12/1991 | Anderson | 602/21 |

Primary Examiner—Robert Bahr
Assistant Examiner—Linda C. M. Dvorak
Attorney, Agent, or Firm—Daniel C. McKown

[57] ABSTRACT

A static orthosis for application to a human patient at an elbow or a knee includes a unitary body composed of a composite material that includes an aluminum endoskeleton molded into a closed cell polyethene foam matrix. The unitary body includes a proximal pad, a distal pad, and an elongated spine connecting the proximal pad and the distal pad. The unitary body is sufficiently stiff that it can be deformed only by deliberate application of strong shaping forces but is not deformed by the casual forces imposed by the patient during normal use of the orthosis. The unitary body is mostly covered by a unitary cover that includes pockets into which the proximal pad and the distal pad fit, and the unitary cover also includes laterally-extending straps for applying the orthosis to the patient. Because of its rigidity and its ability to be deliberately altered, the orthosis is ideally suited for accomplishing a progressive extension of the limb to which it is applied.

10 Claims, 5 Drawing Sheets

STATIC ORTHOSIS FOR ACCOMPLISHING PROGRESSIVE EXTENSION OF A LIMB

BACKGROUND OF THE INVENTION

1. Field of the Invention

The present invention is in the field of medical equipment and specifically relates to a lightweight splint for use on a human elbow or knee for accomplishing a progressive extension of the limb to which it is applied.

2. The Prior Art

The present invention employs a composite body material consisting of an aluminum endo-skeleton molded into a matrix of closed cell polyethylene foam.

The attractiveness of this type of composite material was first recognized in U.S. Pat. No. 3,942,522 issued Mar. 9, 1976 to Kinnier Wilson. The polyethylene cushions the aluminum mesh used and protects the patient from any sharp edges or burrs.

The use of aluminum wires embedded in a polyethylene foam matrix is shown in U.S. Pat. No. 4,928,677 issued May 29, 1990 to Barber and in U.S. Pat. No. 5,058,576 issued Oct. 22, 1991 to Grim, et al.

This composite body material has a number of properties that make it particularly attractive for use in orthoses. It is light in weight, odorless, and does not absorb moisture. Consequently, it does not encourage the growth of bacteria and is easily cleaned with soap and water or alcohol. The aluminum wires or mesh provide a degree of stiffness which is adequate to maintain its shape against casual applied forces, but which is readily deformed by the deliberate application of stronger forces. This permits the orthosis to be supplied in a flat condition and then to be shaped by a skilled practitioner to accommodate the particular shape and size of the patient's limb. Once shaped in this manner, the orthosis has no tendency to revert to its original shape, thereby permitting the splint to "lock in" or retain the degree of extension imparted by the care giver.

The present invention employs this type of composite material to advantage, but the material itself is not the present invention.

Many patients, upon reaching an advanced age, show a tendency for their arms or legs to assume a permanent retraction, i.e., the elbows and knees flex to a contracted position.

When properly used, the orthosis of the present invention can reverse this condition, at least partially, when used in the following manner. A skilled therapist exercises the affected limb by moving it through its entire range of motion and by gently applying an extending force to the limb. Immediately after such exercise, the orthosis of the present invention is applied to hold the limb in the most extended position achieved that day. The same procedure is followed in successive sessions, and the extension gained in each session is maintained by the orthosis. In this way, over a number of days, the orthosis accomplishes a progressive extension of the limb.

As can be appreciated, under such a program of exercise it is not unusual for the limb to spasm, which might cause the patient to retract his limb with sufficient force to alter the shape of the orthosis.

The tendency to spasm is a possible negative effect of this otherwise highly beneficial technique of progressive extension.

Confronted with this potential limitation on the use of the progressive extension technique, the present inventor set out to find a way to counteract the negative effect of spasms.

SUMMARY OF THE INVENTION

It is an objective of the present invention to provide a static orthosis that can be applied without the use of tools for accomplishing progressive extension of a limb.

It is a further objective of the present invention to provide a static progressive-extension orthosis that can be applied without the use of tools and that is light in weight, non-absorbent, odorless, sanitary, and easily cleaned with soap and water or alcohol.

It is a further objective of the present invention to provide a static progressive-extension orthosis having a removable outer cloth cover that consists of a single piece that is removable from the body of the orthosis for cleaning and that is retained on the body by means of a hook-and-loop fastener.

Finally, it is an objective of the present invention to provide a static progressive-extension orthosis that can be left in place on the patient for several hours at a time while producing a progressive extension of a limb and at the same time counteracting the negative effect of spasm in the limb.

From the advantages listed above, it should be clear that the static progressive-extension orthosis of the present invention is particularly advantageous for use on elderly patients and nursing home residents where long-term comfort and ease of care are of foremost importance.

The novel features which are believed to be characteristic of the invention, both as to organization and method of operation, together with further objects and advantages thereof, will be better understood from the following description considered in connection with the accompanying drawings in which several preferred embodiments of the invention are illustrated by way of example. It is to be expressly understood, however, that the drawings are for the purpose of illustration and description only and are not intended as a definition of the limits of the invention.

DETAILED DESCRIPTION OF THE PREFERRED EMBODIMENT

Figure 1:
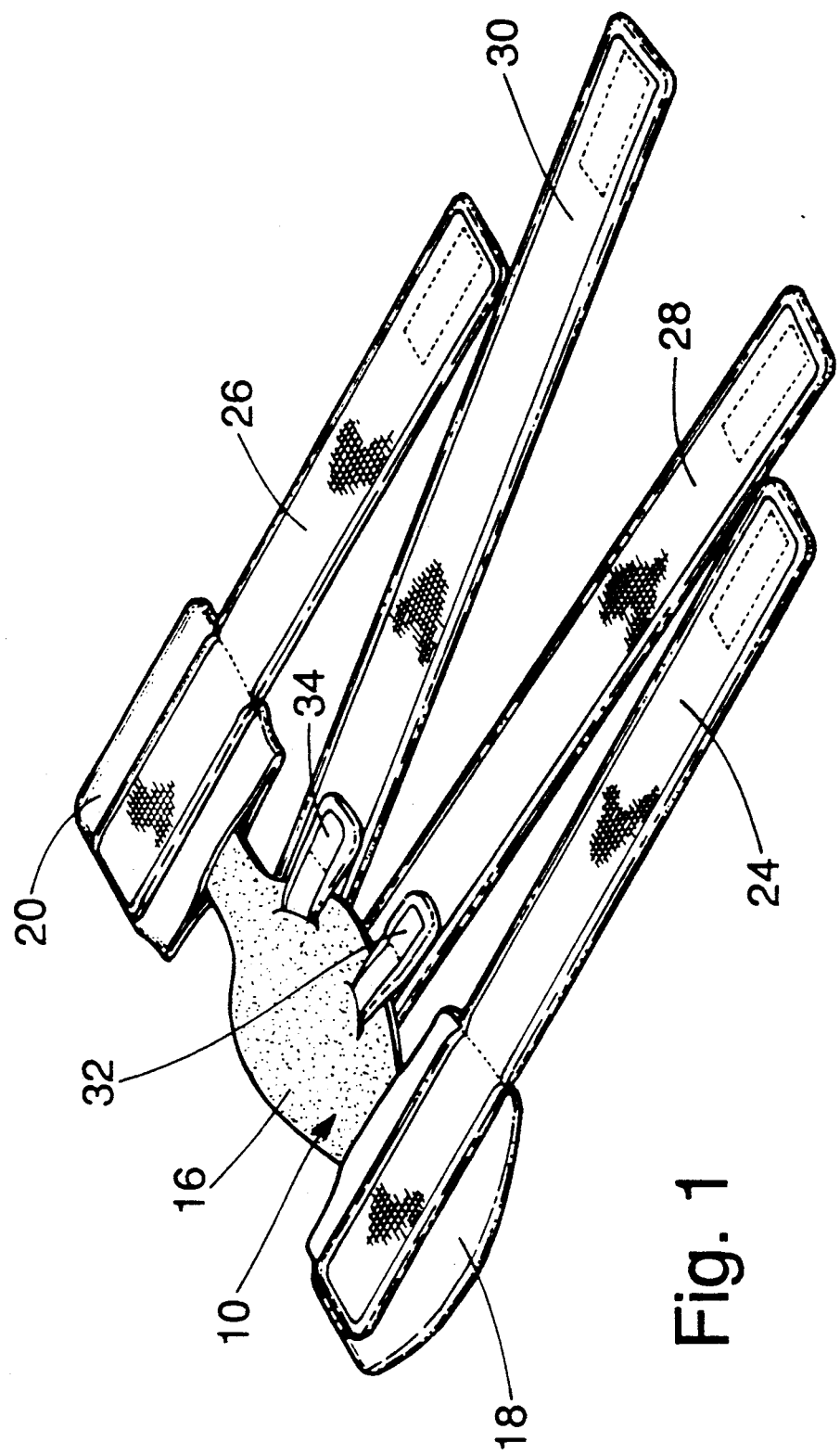
FIG. 1 is a perspective view showing the outer side of a first preferred embodiment of the static progressive-extension orthosis of the present invention suitable for application to an elbow.
Figure 2:
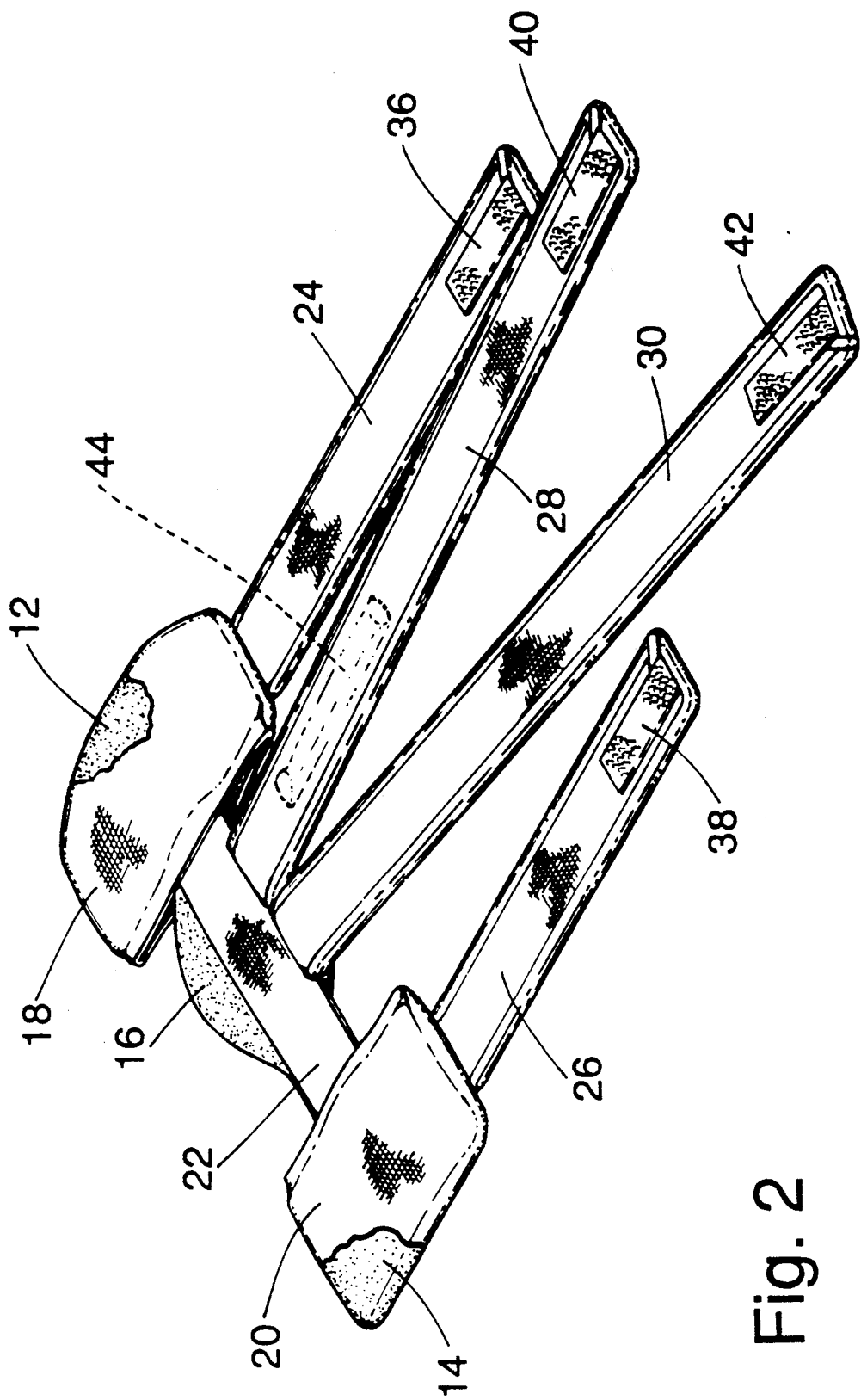
FIG. 2 is a perspective view showing the inner side of the embodiment of FIG. 1.
Figure 3:
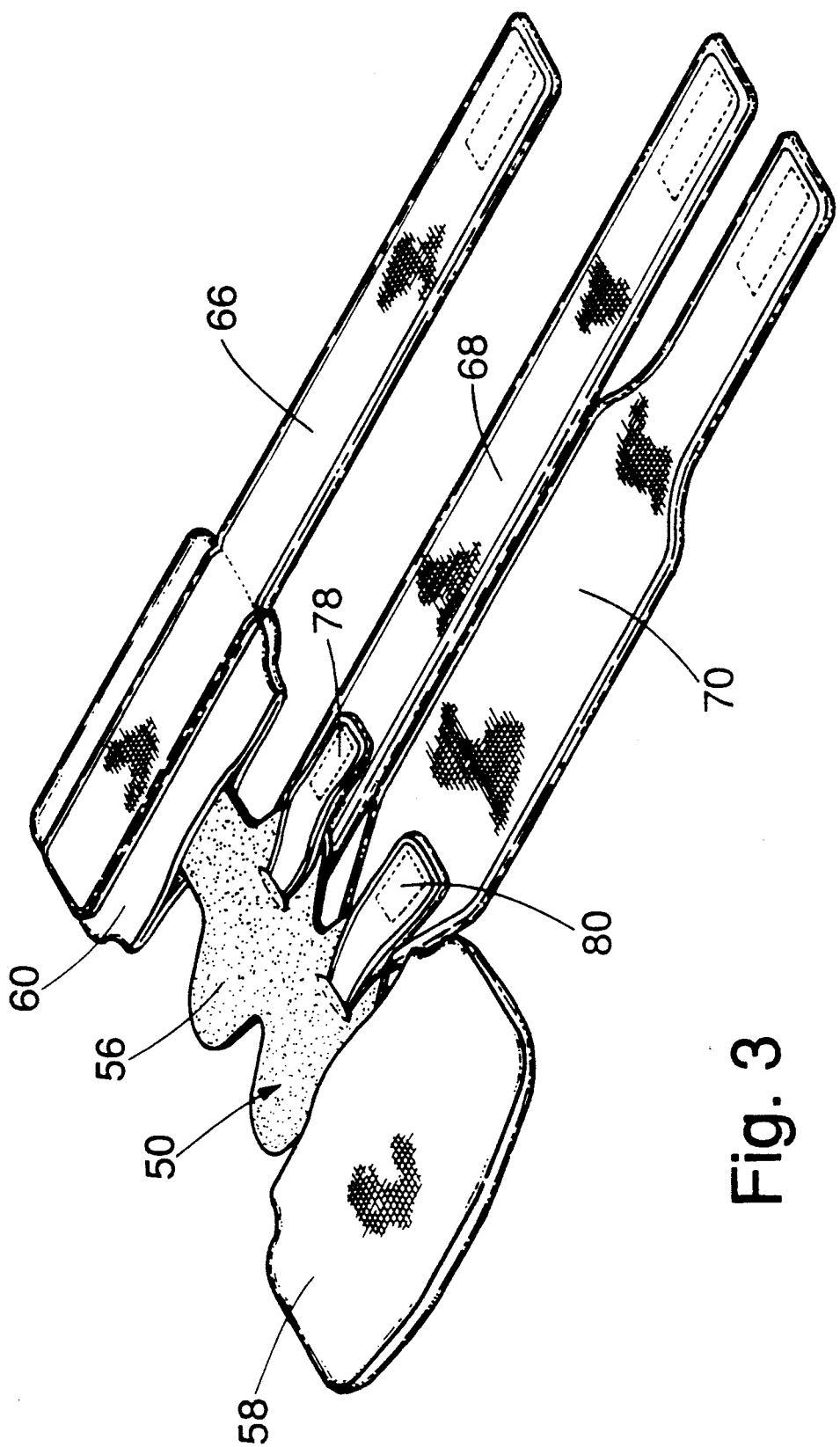
FIG. 3 is a perspective view showing the outer side of a second preferred embodiment of the static progress-extension orthosis of the present invention suitable for application to a knee.
Figure 4:
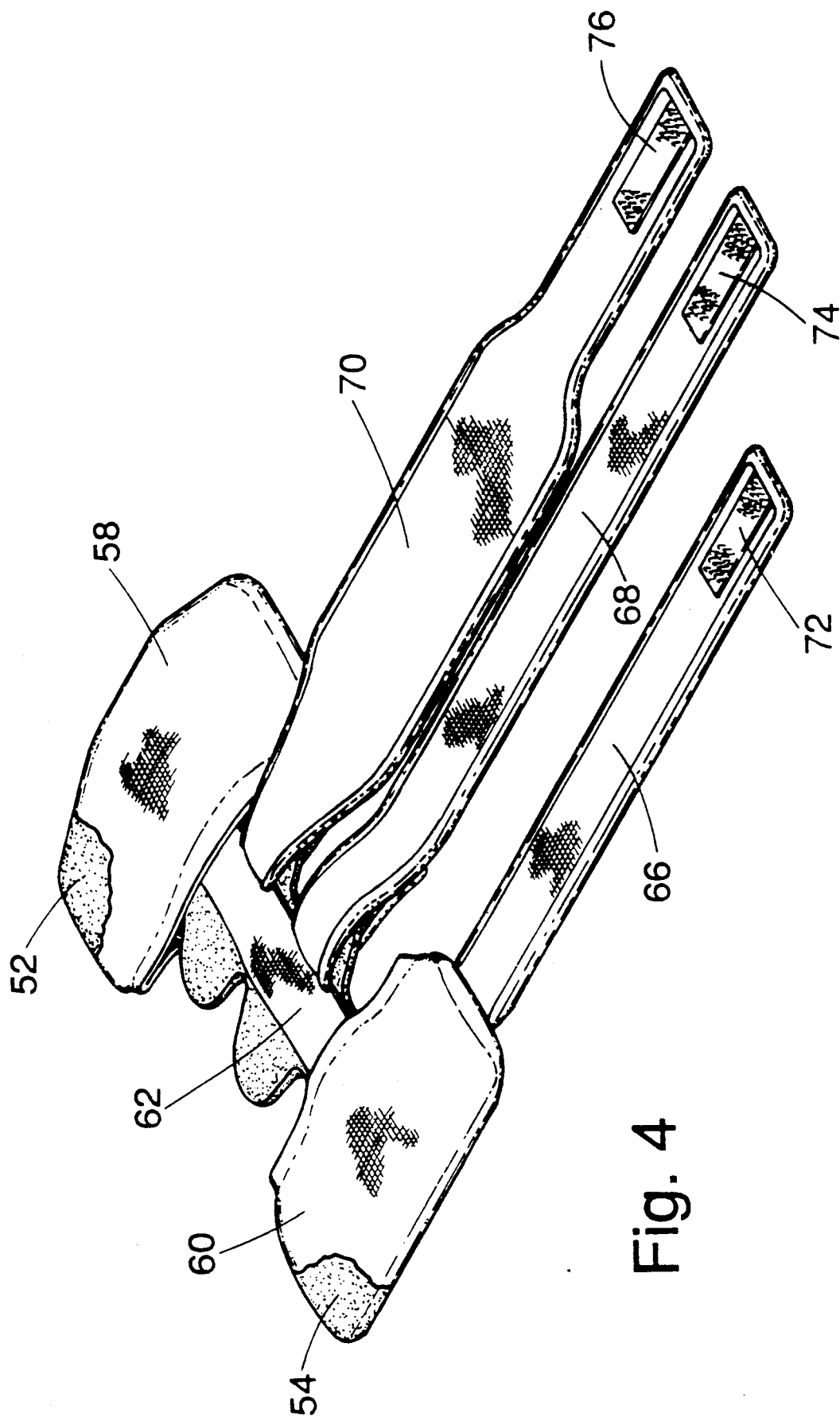
FIG. 4 is a perspective view showing the inner side of the embodiment of FIG. 3.
Figure 5:
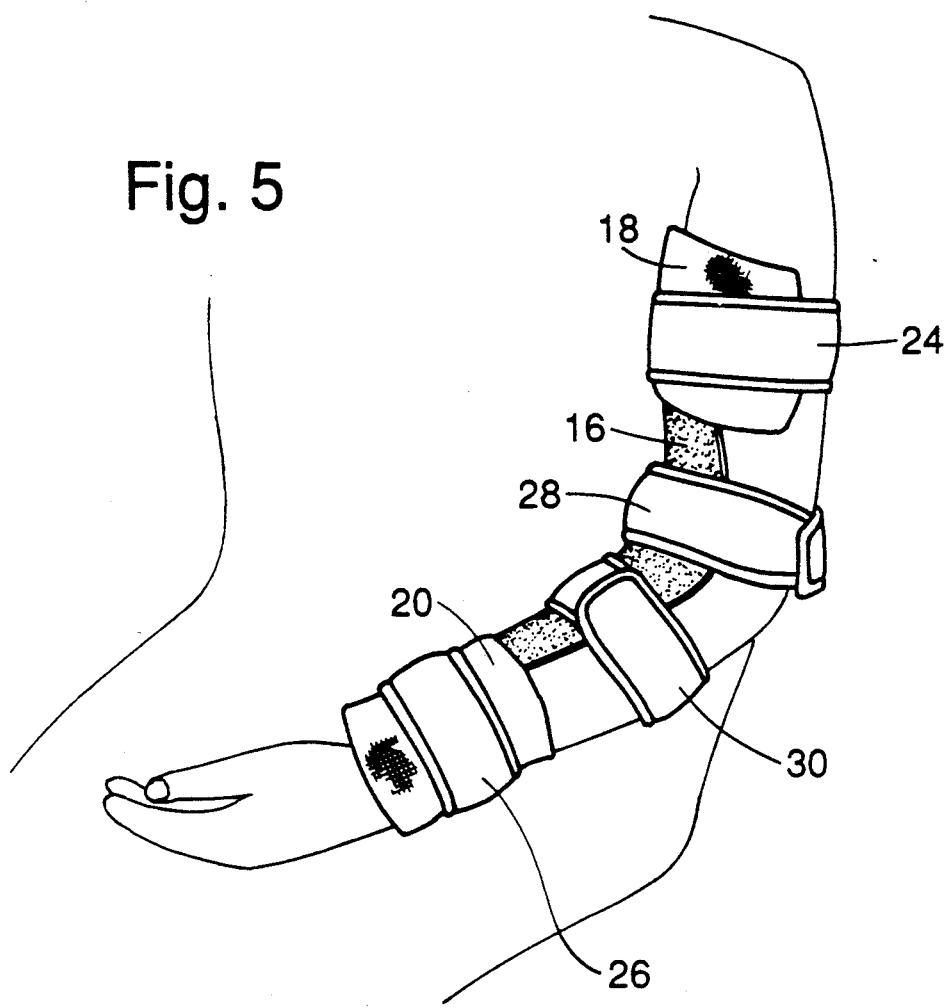
FIG. 5 is a perspective view showing the embodiment of FIGS. 1 and 2 applied to the elbow of a patient; and, FIG. 6 is a perspective view showing the embodiment of FIGS. 3 and 4 applied to the knee of a patient.
Figure 6:
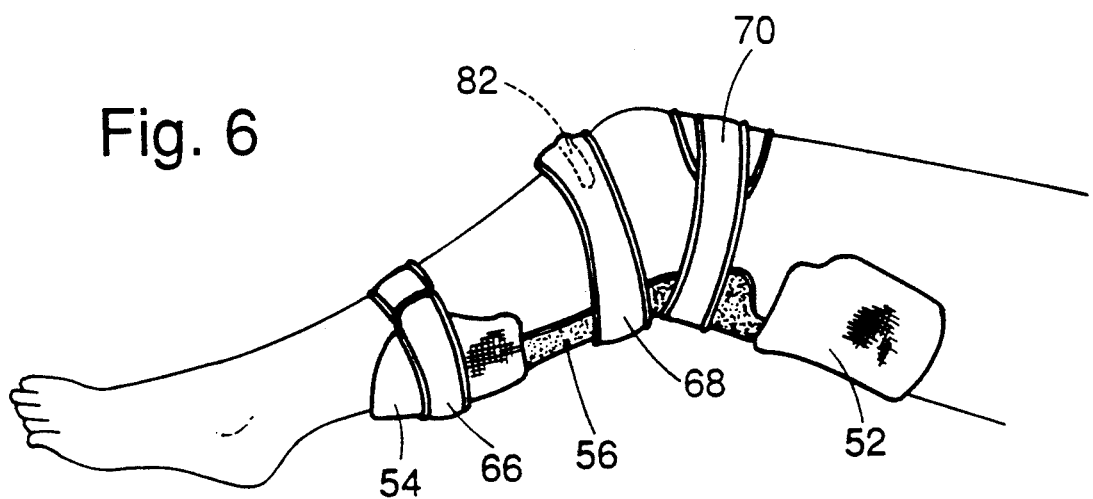

Two preferred embodiments of the present invention are described below. The first preferred embodiment shown in FIGS. 1, 2 and 5 is for application to the elbow of a human patient, while the second preferred embodiment shown in FIGS. 3, 4 and 6 is intended for application to the knee of a human patient. As will be seen below, the two embodiments are generally similar but differ in details.

Turning now to the embodiment of FIGS. 1 and 2, the static progressive-extension orthosis of FIGS. 1 and 2 consists of two major parts, a unitary body 10, and a unitary cover that covers portions of the unitary body and includes a number of straps. The unitary body 10 is a composite material consisting of an aluminum endo-skeleton molded into a matrix of closed cell polyethylene foam. The aluminum endo-skeleton is sufficiently stiff that it can be deformed only by deliberate manual application of strong forces. It is not deformed by the casual forces imposed by the patient during normal use of the static orthosis. Thus, the shape of the orthosis is established by the therapist, without the use of tools, and that shape is maintained by the stiffness of the unitary body 10 of the orthosis during normal use.

The unitary body 10 includes a proximal pad 12 and a distal pad 14 that are connected by a spine 16. Corresponding to these parts, the unitary cover includes a proximal pocket 18 that covers and encloses the proximal pad 12, a distal pocket 20 that covers and encloses the distal pad 14, and a spine strap 22 that interconnects the proximal pocket 18 and the distal pocket 20. The open sides of the proximal pocket 18 and the distal pocket 20 face each other. In the preferred embodiment, the spine strap 22 is elastic to facilitate placing the unitary cover on the unitary body; however, in another embodiment the first strap may be inelastic, necessitating greater bending of the endo-skeleton.

In the preferred embodiment, the proximal pad 12 has a different size and shape from the distal pad 14, and the proximal pocket 18 fits snugly on the proximal pad 12 while the distal pocket 20 fits snugly on the distal pad 14. Accordingly, it is not possible to put the unitary cover onto the unitary body in any other than the correct manner.

In the embodiment of FIGS. 1 and 2, the additional straps 24 and 26 extend laterally from the proximal pocket 18 and the distal pocket 20 respectively.

In addition, the straps 28 and 30 extend laterally from the spine portion 16 of the unitary body. The ends of the straps 28 and 30 pass through slits in the spine 16 and are then anchored to the main portion of the straps 28 and 30 by hook-and-loop fasteners 32 and 34, respectively. Additionally, the straps 28 and 30 are sewn to the spine strap 22 to prevent them from becoming misplaced or interchanged when the cover is washed.

Hook-and-loop fasteners 36, 38, 40 and 42 are provided at the free ends of the straps 24, 26, 28, and 30 respectively for use in closing these straps upon themselves to form loops that encircle the patient's arm.

An important feature of the first embodiment of the present invention is the provision of a stay 44 that is sewn into a small pocket in the strap 28. In the preferred embodiment, the stay consists of a short length of a thick-walled plastic tubing oriented parallel to the strap 28. The tightness of the strap 28 pulls against the ends of the stay forcing it to curve around the arm of the patient. The elastic restoring force of the stay exerts a mild or gentle pressure against the fascia of the triceps tendon of the patient's arm, thereby counteracting possible muscle spasm.

FIG. 5 shows the orthosis of the embodiment of FIGS. 1 and 2 applied to the elbow of a patient. The spine 16 has been bent approximately 90 degrees, and the proximal pad 12 and the distal pad 14 have been shaped to partially encircle the arm of the patient. Thereafter, the laterally-extending straps have been wrapped around the patient's arm and the hook-and-loop fasteners at the free ends of the straps have been attached to the exposed surface of the straps.

As mentioned above, there is a tendency among elderly and frail patients for the elbow to be held in a flexed position, and after a sufficient length of time the range of motion of the arm is severely limited. The static orthosis of the present invention is quite useful in such a condition for bringing about a progressive extension of the arm and thereby greatly improving its range of motion. Prior to applying the orthosis of the present invention, a physical therapist or care professional will exercise the arm by moving it repeatedly through its entire range of motion and trying gently to extend the range of motion of the arm. At the end of the exercise session, the care giver applies the orthosis of the present invention in such a manner that it holds the arm in a comfortable position at the limit of its extension. This prevents the arm from retracting which would result in the elbow giving up the extent of motion gained in the exercise. At the next exercise session, the arm is again exercised with a view toward increasing its maximum extension. Normally the maximum extension of the arm will be greater after the second session than it was after the first exercise session, and the orthosis is again applied to the arm after being adjusted to the greater angle of extension. In this manner, the maximum angle of extension is progressively increased from one exercise session to the next, and at each stage, the increased extension is held by use of the orthosis.

Turning now to the embodiment of FIGS. 3, 4 and 6, which is intended to be applied to the knee of a human patient, it is apparent that the embodiment includes only three straps instead of the four straps used in the embodiment of FIGS. 1 and 2.

The embodiment of FIGS. 3 and 4 includes a unitary body 50 having a proximal pad 52 and a distal pad 54 that are connected by a spine 56. The material of which the unitary body 50 is composed is the same as the material of which the unitary body 10 of FIGS. 1 and 2 is composed.

A proximal pocket 58 fits snugly over the proximal pad 52, and a distal pocket 60 fits snugly over a distal pad 54. The open ends of the pockets face each other as shown in FIGS. 3 and 4, and the pockets 58 and 60 are connected by a spine strap 62. The straps 68 and 70 are sewn to the spine strap 62 so that the proximal pocket 58, the distal pocket 60, the spine strap 62, and the additional straps 66, 68 and 70 are all sewn together to guard against their coming loose, being misplaced, or being replaced in the wrong position. These parts, which together make up the unitary cover of the body 50, are made of fabric and are washable.

As in the embodiment of FIGS. 1 and 2, the free ends of the straps 66, 68, 70 are provided with hook-and-loop fasteners 72, 74 and 76 respectively, which permit rapid fastening of the straps without the problems inherent in buckles or the like.

Hook-and-loop fasteners are also used to prevent the ends 78 and 80 of the straps 68 and 70 from being pulled loose from the spine 56.

FIG. 6 shows the static progressive-extension orthosis of FIGS. 3 and 4 applied to the knee of a patient. In accordance with the preferred embodiment of the invention, a stay 82 is provided in the strap 68 for the purpose of exerting a gentle pressure across the knee just below the kneecap. The use of this stay opposes any tendency the leg might have to contract.

Thus, there has been described a static progressive-extension orthosis that is lightweight, sanitary, easily applied and removed, and comparatively inexpensive. These features make it ideal for application to elderly or frail patients for the purpose of accomplishing a progressive extension of the limb to which it is applied.

The foregoing detailed description is illustrative of several embodiments of the invention, and it is to be understood that additional embodiments thereof will be obvious to those skilled in the art. The embodiments described herein together with those additional embodiments are considered to be within the scope of the invention.

What is claimed is:

1. A static progressive-extension orthosis for application to a limb of a human patient at an elbow or knee, comprising:
    a unitary body including
        a proximal pad,
        a distal pad,
        an elongated spine connecting said proximal pad and said distal pad; and,
    a unitary cover including
        a proximal pocket covering said proximal pad,
        a distal pocket covering said distal pad,
        a spine strap extending along said spine connecting said proximal pocket and said distal pocket,
        at least two additional straps attached to said unitary cover and extending perpendicular to said spine strap so as to encircle the limb to which the static progressive-extension orthosis is applied.

2. The static progressive-extension orthosis of claim 1 wherein said proximal pad has a different size and shape from said distal pad and wherein said proximal pocket and said distal pocket conform in size and shape to said proximal pad and said distal pad respectively, whereby said unitary cover fits on said unitary body in only one way.

3. The static progressive-extension orthosis of claim 1 wherein said unitary body is composed of a composite material that includes an aluminum endo-skeleton embedded within a closed cell polyethylene plastic.

4. The static progressive-extension orthosis of claim 3 wherein said aluminum endo-skeleton is sufficiently stiff that it can be deformed only by deliberate manual application of strong forces but is not deformed by casual forces imposed by the patient during normal use of the static progressive-extension orthosis, whereby the static progressive-extension orthosis can be fitted to a patient without the use of tools and will hold during normal use the shape imparted to it in the fitting.

5. A static progressive-extension orthosis for application to a limb of a human patient at an elbow or knee, comprising:
    a unitary body including
        a proximal pad,
        a distal pad,
        an elongated spine connecting said proximal pad arid said distal pad; and,
    a unitary cover including
        a proximal pocket covering said proximal pad,
        a distal pocket covering said distal pad,
        a spine strap extending along said spine and connecting said proximal pocket and said distal pocket,
        at least two additional straps attached to said unitary cover and extending perpendicular to said spine strap so as to encircle the limb to which the static progressive-extension orthosis is applied,
        one of said at least two additional straps including a stay so located as to bear gently against a particular region of the limb when the static progressive-extension orthosis has been applied to the limb.

6. The static progressive-extension orthosis of claim 5 wherein said proximal pad has a different size and shape from said distal pad and wherein said proximal pocket and said distal pocket conform in size and shape to said proximal pad and said distal pad respectively, whereby said unitary cover fits on said unitary body in only one way.

7. The static progressive-extension orthosis of claim 5 wherein said unitary body is composed of a composite material that includes an aluminum endo-skeleton embedded within a closed cell polyethylene plastic.

8. The static progressive-extension orthosis of claim 7 wherein said aluminum endo-skeleton is sufficiently stiff that it can be deformed only by deliberate manual application of strong forces but is not deformed by casual forces imposed by the patient during normal use of the static progressive-extension orthosis, whereby the static progressive-extension orthosis can be fitted to a patient without the use of tools and will hold during normal use the shape imparted to it in the fitting.

9. The static progressive-extension orthosis of claim 5 wherein said stay is adapted to bear gently against the fascia of the triceps tendon and wherein said static progressive-extension orthosis is applied at the elbow of the patient.

10. The static progressive-extension orthosis of claim 5 wherein said stay is adapted to bear gently just below the kneecap and wherein said static progressive-extension orthosis is applied at the knee of the patient.

* * * * *